(12) United States Patent
Winkler et al.

(10) Patent No.: US 11,669,608 B2
(45) Date of Patent: *Jun. 6, 2023

(54) SYSTEMS AND METHODS FOR CONTROLLING UNITS FOR A SCALE

(71) Applicant: Pelstar, LLC, McCook, IL (US)

(72) Inventors: Mark Winkler, McCook, IL (US); Ken Harris, McCook, IL (US); Rosalyn Ben-Chitrit, McCook, IL (US)

(73) Assignee: Pelstar, LLC, McCook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/832,362

(22) Filed: Jun. 3, 2022

(65) Prior Publication Data

US 2022/0292175 A1   Sep. 15, 2022

Related U.S. Application Data

(63) Continuation of application No. 16/263,395, filed on Jan. 31, 2019, now Pat. No. 11,354,393.

(60) Provisional application No. 62/624,943, filed on Feb. 1, 2018.

(51) Int. Cl.
   *G06F 21/33* (2013.01)
   *G06F 21/31* (2013.01)
   *G16H 10/60* (2018.01)

(52) U.S. Cl.
   CPC .............. *G06F 21/33* (2013.01); *G06F 21/31* (2013.01); *G16H 10/60* (2018.01)

(58) Field of Classification Search
   USPC ........................................................ 726/19
   See application file for complete search history.

(56) References Cited

U.S. PATENT DOCUMENTS

| 5,442,146 A | 8/1995 | Bell et al. |
| 7,550,682 B2 | 6/2009 | Lawler et al. |
| 8,704,110 B2 * | 4/2014 | Forshaw ............... G01G 19/44 |
| | | 600/300 |

(Continued)

FOREIGN PATENT DOCUMENTS

| AU | 2016201310 A1 * | 3/2016 | ............. G06F 21/31 |
| CA | 2767723 C * | 8/2018 | ............. G06Q 10/04 |
| CN | 105804517 A * | 7/2016 | |

*Primary Examiner* — Sakinah White Taylor
(74) *Attorney, Agent, or Firm* — Michael Best & Friedrich LLP

(57) ABSTRACT

Systems and methods for controlling measurement units for a medical scale. One system includes a removable head unit configured to couple to a medical scale platform. The removable head unit includes a human machine interface (HMI) and an electronic processor coupled to the human machine interface. The electronic processor is configured to receive, via the HMI, a first user input selecting a permanent lock mode. The electronic processor is configured to, in response to receiving the user input, present a first authentication request and receive a second user input including a first authentication token. The electronic processor is configured to, when the first authentication token is valid, present a measurement unit selection prompt. The electronic processor is configured to receive a second user input selecting a measurement unit and, in response to receiving the second user input, activate the permanent lock mode based on the selected measurement unit.

20 Claims, 8 Drawing Sheets

(56) References Cited

U.S. PATENT DOCUMENTS

| | | |
|---|---|---|
| 10,050,787 B1 | 8/2018 | Johansson et al. |
| 10,679,342 B2 * | 6/2020 | Nowicki ................ H04N 23/80 |
| 11,354,393 B2 | 6/2022 | Winkler et al. |
| 2001/0043702 A1 | 11/2001 | Elteto et al. |
| 2003/0055406 A1 | 3/2003 | Lebel et al. |
| 2003/0191719 A1 | 10/2003 | Ginter et al. |
| 2004/0101299 A1 | 5/2004 | Matsumoto et al. |
| 2008/0001725 A1 | 1/2008 | White et al. |
| 2008/0223625 A1 | 9/2008 | Lawler et al. |
| 2013/0131862 A1 | 5/2013 | Jefferies et al. |
| 2014/0283007 A1 | 9/2014 | Lynch |
| 2017/0076115 A1 | 3/2017 | Ishihara et al. |
| 2019/0274565 A1 * | 9/2019 | Soli .................... A61B 5/02438 |
| 2021/0010854 A1 | 1/2021 | Ohler et al. |
| 2021/0298817 A1 | 9/2021 | Schwarz |

\* cited by examiner

SYSTEMS AND METHODS FOR CONTROLLING UNITS FOR A SCALE

CROSS-REFERENCE TO RELATED APPLICATION

The present application is a continuation of and claims the benefit of the filing date of co-pending U.S. patent application Ser. No. 16/263,395, filed Jan. 31, 2019, which claims priority to U.S. Provisional Patent Application Ser. No. 62/624,943, filed Feb. 1, 2018.

FIELD

The present application relates to systems and methods for controlling the display of measurements by scales and, more particularly, medical scales.

SUMMARY

Medical scales are used in healthcare environments to measure the weight of a patient. A patient's weight can provide important or useful information to, for example, detect fluid retention, calculate proper medication dosages, screen for malnutrition, etc. It is therefore desirable for medical scales to provide accurate weight measurements to healthcare professionals and other users. Some healthcare determinations are made taking into account the unit of measurement used by the scale.

Because medical scales are used to provide important or useful information for patient care, medical scales may be calibrated regularly, for example, using reference weights or calibration devices. The calibration process can be expensive (for example, about 35-90% of the cost of a new scale per calibration) and time-consuming, especially for a facility with numerous scales. Calibration data is stored in the electronics of the scale, often in a non-volatile random access memory (NVRAM).

In certain countries, patients are often more likely to understand their weight in terms of the one system of units (for example, in the United States, the Imperial system, that is, in pounds (lbs.)), whereas healthcare professionals may be more likely to require the patient weight measurement in a different system of units (the metric system, in kilograms (kg)). As such, electronic medical scales are often capable of displaying weight measurements in pounds, kilograms, or both.

Some healthcare professionals require that the weight of a patient be expressed solely in one system of units (for example, in kilograms because drug dosing is typically provided in terms of milligrams per kilogram of body weight). However, when a scale is capable of providing patient weight measurements in different units, it is possible that the patient's weight may be recorded incorrectly (for example, by recording with incorrect units, by incorrectly converting from one unit to the other, etc.).

To address these and other needs, some medical scales (for example, used in a critical care environment) are only capable of providing patient weight using a single unit type (that is, either only in pounds or only in kilograms). However, such scales sacrifice flexibility because they cannot be made to display weight measurements in another unit type and, thus, cannot be used in applications in which that capability is desirable (for example, in a primary care physician's office).

This may cause healthcare providers (for example, facilities with both critical care and primary care) to waste resources. For example, providers may be forced to purchase new scales instead of re-purposing existing scales. In another example, extra computer or other resources may have to be used to perform unit conversions.

Some scales may be repurposed by re-burning their firmware to turn them from one type of scale to another. However, re-burning, re-flashing, or replacing the scale's software also erases the scale's calibration, requiring the scale to again be calibrated before use and, thereby, increasing costs to the scale user.

Independent embodiments described herein provide, among other things, systems and methods for permanently locking medical scales into a measurement unit (for example, kilograms or pounds) while allowing factory reset and maintaining the scale's calibration. The medical scale may also be operable in more than one mode relating to the unit of measurement.

In one independent embodiment, an electronic scale may be operable to measure and display weight in different units of measurement (for example, kilograms, pounds, etc.) and may be configured with a permanent lock mode, also referred to herein as an "Everlock™" mode. The Everlock™ mode, when activated, "permanently" locks the scale into a single selected unit of measurement. When activated by a scale user, the Everlock™ mode functions to disable features that normally allow scale users to select between units of measurement. Accordingly, once a user of the scale activates the Everlock™ mode, the user is not able to deactivate the mode. In the embodiments described herein, the Everlock™ mode causes the scale to be permanently locked, at least from the scale user's point of view, into displaying weight measurements in the selected units. Such embodiments provide advantages over existing single-unit scales. For example, the "lockable" scale provides flexibility for the user in determining how to use the scale.

It should be noted that, as used herein with regard to aspects of the described embodiments, the terms "permanent" and "permanently" are not used to indicate a state that is unchangeable in perpetuity. Rather, the terms "permanent" and "permanently" are used to indicate a state (for example, being locked into a unit of measurement) that is established without a predetermined end point, and which can only be altered under certain circumstances. In some aspects, "permanent" or "permanently" may mean that the locked unit of measurement may only be unlocked in a limited number ways (for example, in only one way). For example, in some aspects, it may be possible for the Everlock™ mode to be deactivated (for example, by factory technicians using specialized hardware, software, or combinations thereof, unavailable to end users) to allow the scale to be again used with its full functionality.

Because the calibration of scales is both costly and important to the proper functioning of the scales, in some embodiments, calibration data stored in the scale may not be overwritten or erased when the Everlock™ mode is activated or deactivated. In embodiments in which the Everlock™ mode is factory-resettable, only a removable head unit or other detachable electronic portion of the scale need be sent to the manufacturer in order to deactivate the Everlock™ mode. This allows the mechanical portions of the scale to remain at the user site, limiting shipping costs, resulting in a much faster turn-around time compared to shipping the entire scale, reducing the possibility that movement (for example, by packaging and shipping) of the scale might alter the scale's calibration, etc.

Therefore, using such embodiments, medical scales are provided that may be permanently locked into a particular unit of measurement by a scale user, and reset (for example, by the factory) to allow changes to the units used, while maintaining the scale's calibration to ensure accurate readings, regardless of the measurement units in use. Such embodiments may reduce the inventory requirements of suppliers, distributors, and larger scale users (for example, medical clinics, hospitals, etc.), because all such scales are capable of multiple measurement unit mode operation, including a permanently locked measurement unit mode of operation. Such embodiments make it easier for scale users to deploy a new scale into their operation. The flexibility of being able to select what units a scale will use after the scale is put into service eliminates the need to determine with certainty what type (unit-wise) of scale is needed prior to ordering. Such embodiments may also reduce the need for multiple software versions, as a single software version can provide multi-measurement unit and unit-locked (for example, kilogram-locked, pound-locked) operation modes.

In another independent embodiment, an electronic scale may be operable in multiple measurement unit modes to measure and display weight. In one mode (for example, a "Toggle" mode), the user may select the measurement unit (for example, kilograms) and may modify the selection to another measurement unit (for example, pounds). In another mode, the user may permanently lock the measurement unit (for example, the Everlock™ mode). The scale may include another mode (for example, the "Unit Lock" mode), in which the measurement unit is selectively locked and may be unlocked by the user. In some modes, the scale may be able temporarily display another measurement unit (for example, "Unit View").

Other independent aspects of the invention may become apparent by consideration of the detailed description and accompanying drawings.

DETAILED DESCRIPTION

Figure 1:
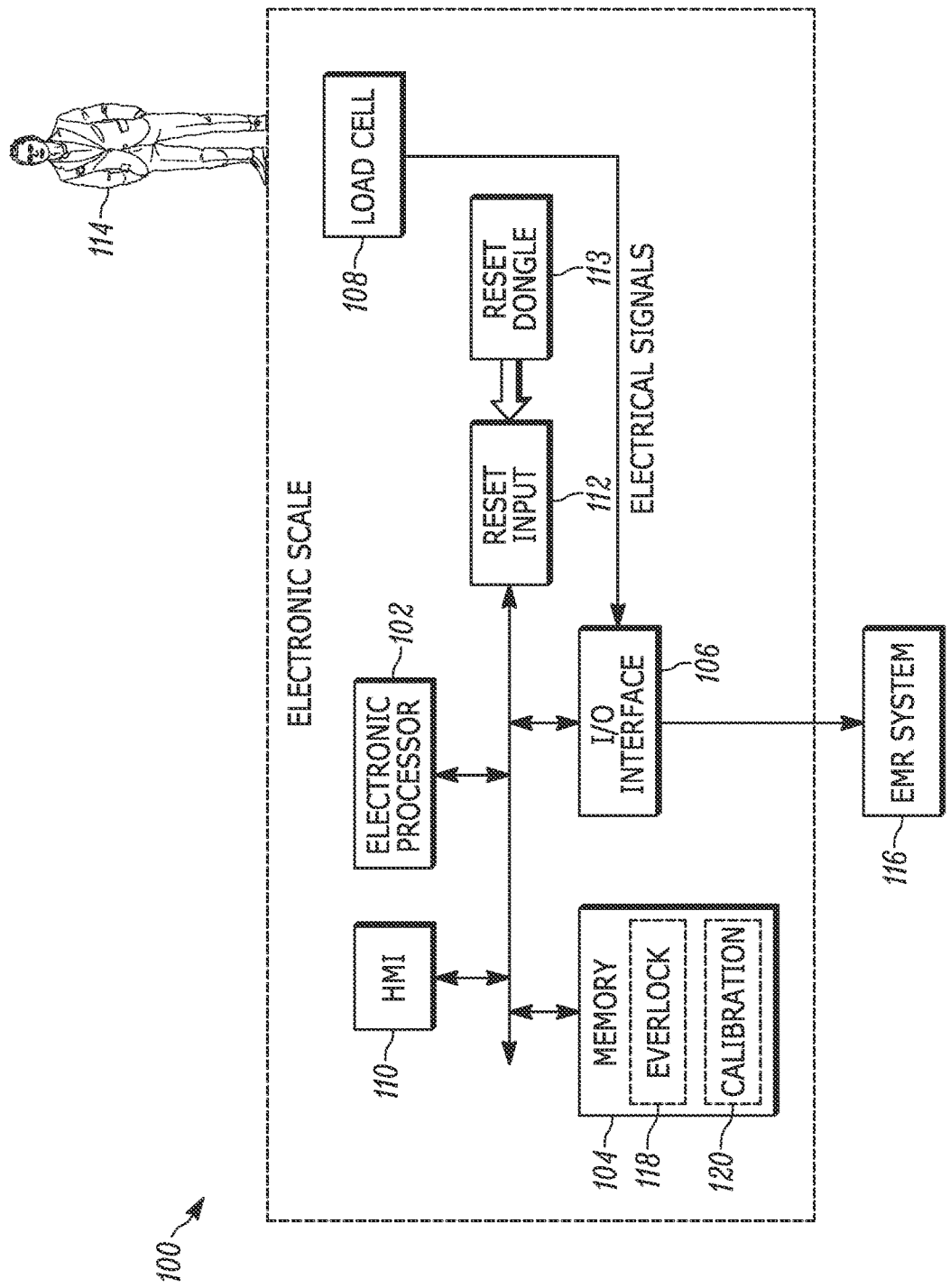
FIG. 1 is a block diagram of a scale, according to some independent embodiments.

Before any independent embodiments are explained in detail, it is to be understood that the embodiments presented herein are not limited in their application to the details of construction and the arrangement of components set forth in the following description or illustrated in the following drawings. The independent embodiments presented herein are capable of being practiced or of being carried out in various ways. Also, it is to be understood that the phraseology and terminology used herein is for the purpose of description and should not be regarded as limiting.

The use of "including," "comprising," or "having" and variations thereof herein is meant to encompass the items listed thereafter and equivalents thereof as well as additional items. The terms "mounted," "connected," and "coupled" are used broadly and encompass both direct and indirect mounting, connecting, and coupling. Further, "connected" and "coupled" are not restricted to physical or mechanical connections or couplings, and can include electrical connections or couplings, whether direct or indirect. Also, electronic communications and notifications may be performed using any known means including wired connections, wireless connections, etc.

Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way but may also be configured in ways that are not listed.

It should also be noted that a plurality of hardware and software based devices, as well as a plurality of different structural components may be used to implement the embodiments. In addition, it should be understood that embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (for example, stored on non-transitory computer-readable medium) executable by one or more processors. As such, it should be noted that a plurality of hardware and software based devices, as well as a plurality of different structural components may be utilized to implement the invention. For example, "control units" and "controllers" described in the specification can include one or more processors, one or more memory modules including non-transitory computer-readable medium, one or more input/output interfaces, and various connections (for example, a system bus) connecting the components.

For ease of description, some or all of the exemplary systems presented herein are illustrated with a single exemplar of each of its component parts. Some examples may not describe or illustrate all components of the systems. Other exemplary embodiments may include more or fewer of each of the illustrated components, may combine some components, or may include additional or alternative components.

FIG. 1 illustrates an exemplary independent embodiment of a scale 100 (for example, a medical scale) used to measure the weight of a patient 114. The scale 100 may include various digital and analog components, which for brevity are not described herein and which may be implemented in hardware, software, or a combination of both. Components of the scale 100 may be similar to the components illustrated and described in U.S. Pat. No. 7,550,682, issued Jun. 23, 2009, the entire contents of which are hereby incorporated by reference.

The scale 100 includes an electronic processor 102, a memory 104, an input/output interface 106, a load cell 108, a human machine interface (HMI) 110, and a reset input 112. The illustrated components, along with other various modules and components, are coupled to each other by or through one or more control or data buses that enable communication therebetween. The use of control and data buses for the interconnection between and exchange of information among the various modules and components would be apparent to a person skilled in the art in view of the description provided herein.

Figure 2A:
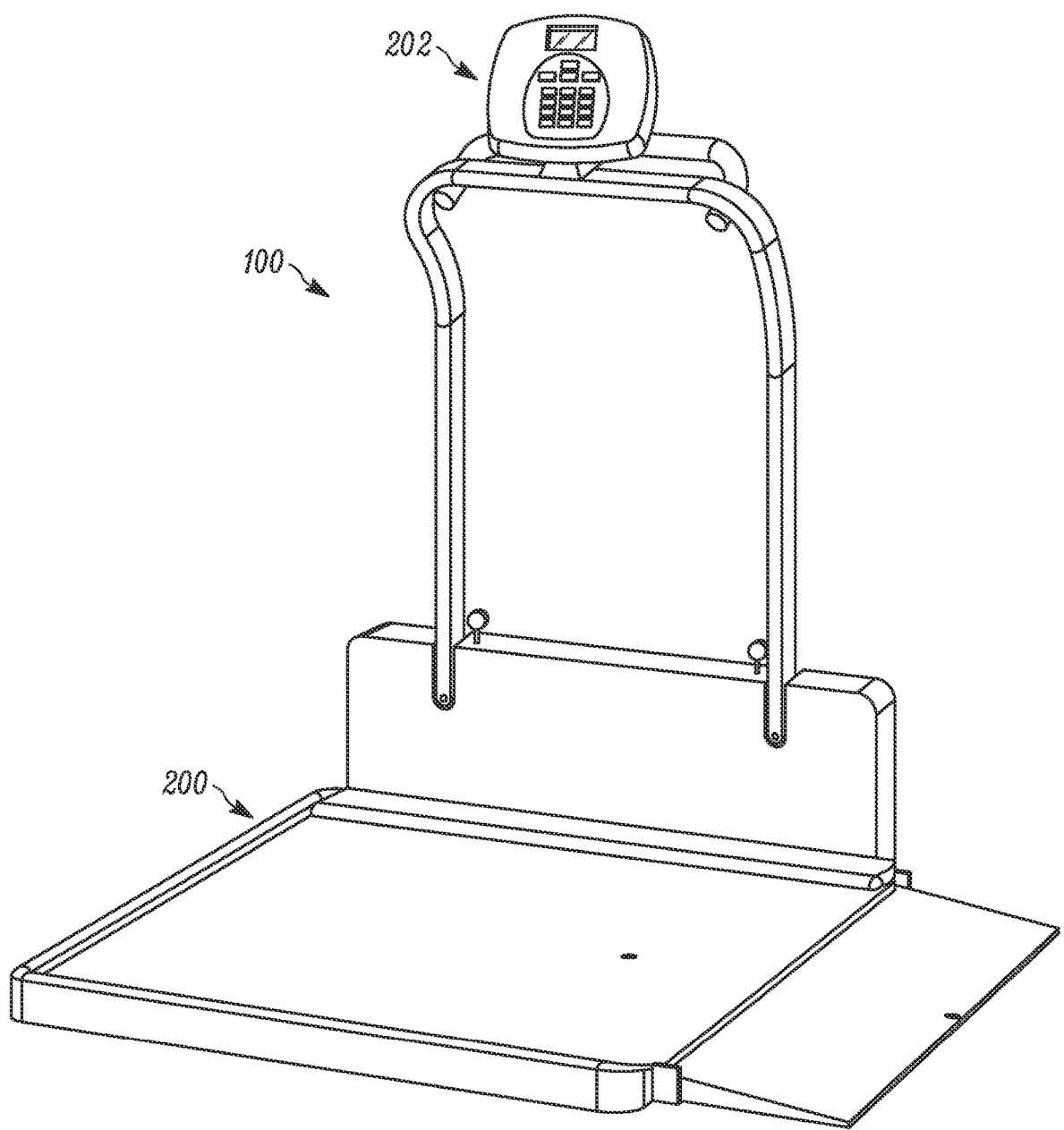
FIGS. 2A-2C depict example embodiments of the scale of FIG. 1.
Figure 2B:
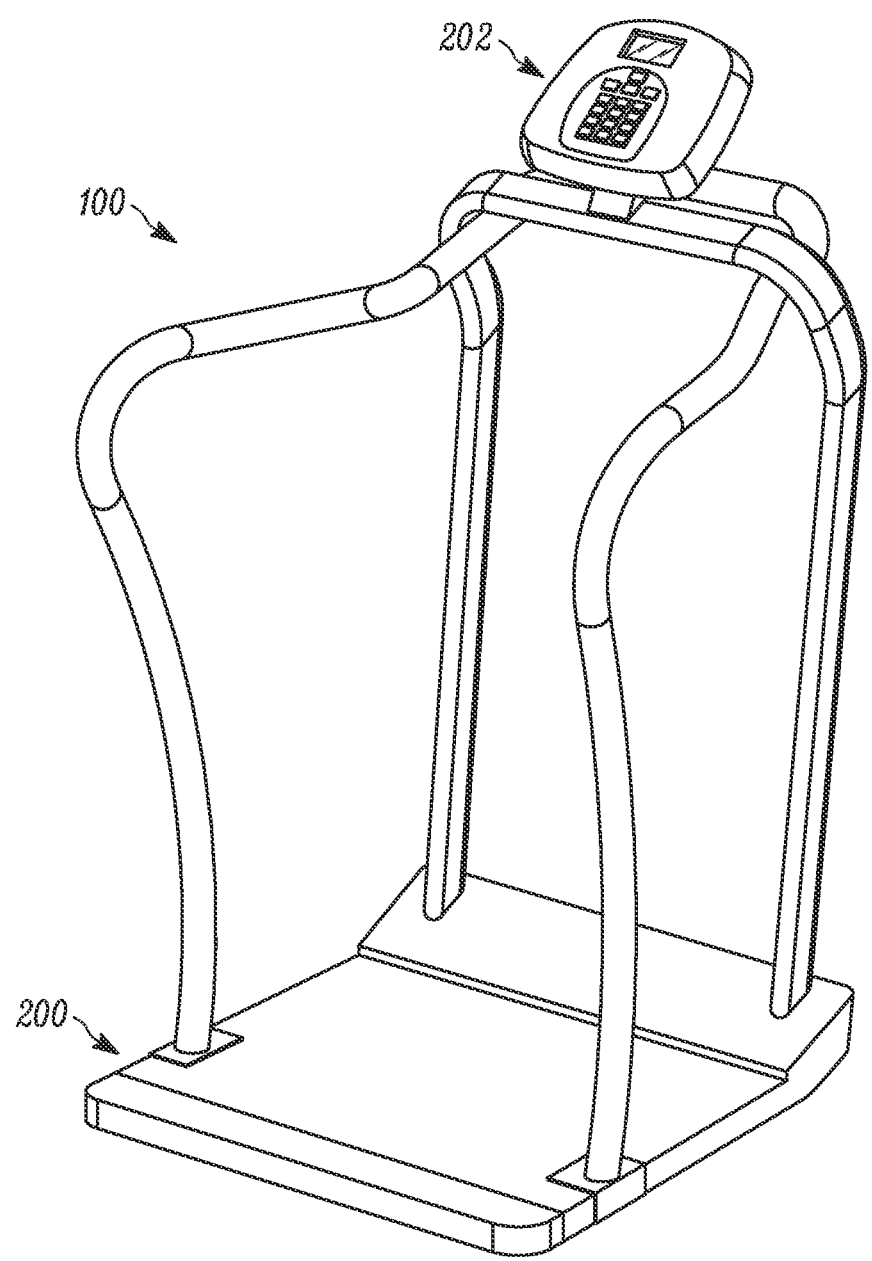
Figure 2C:
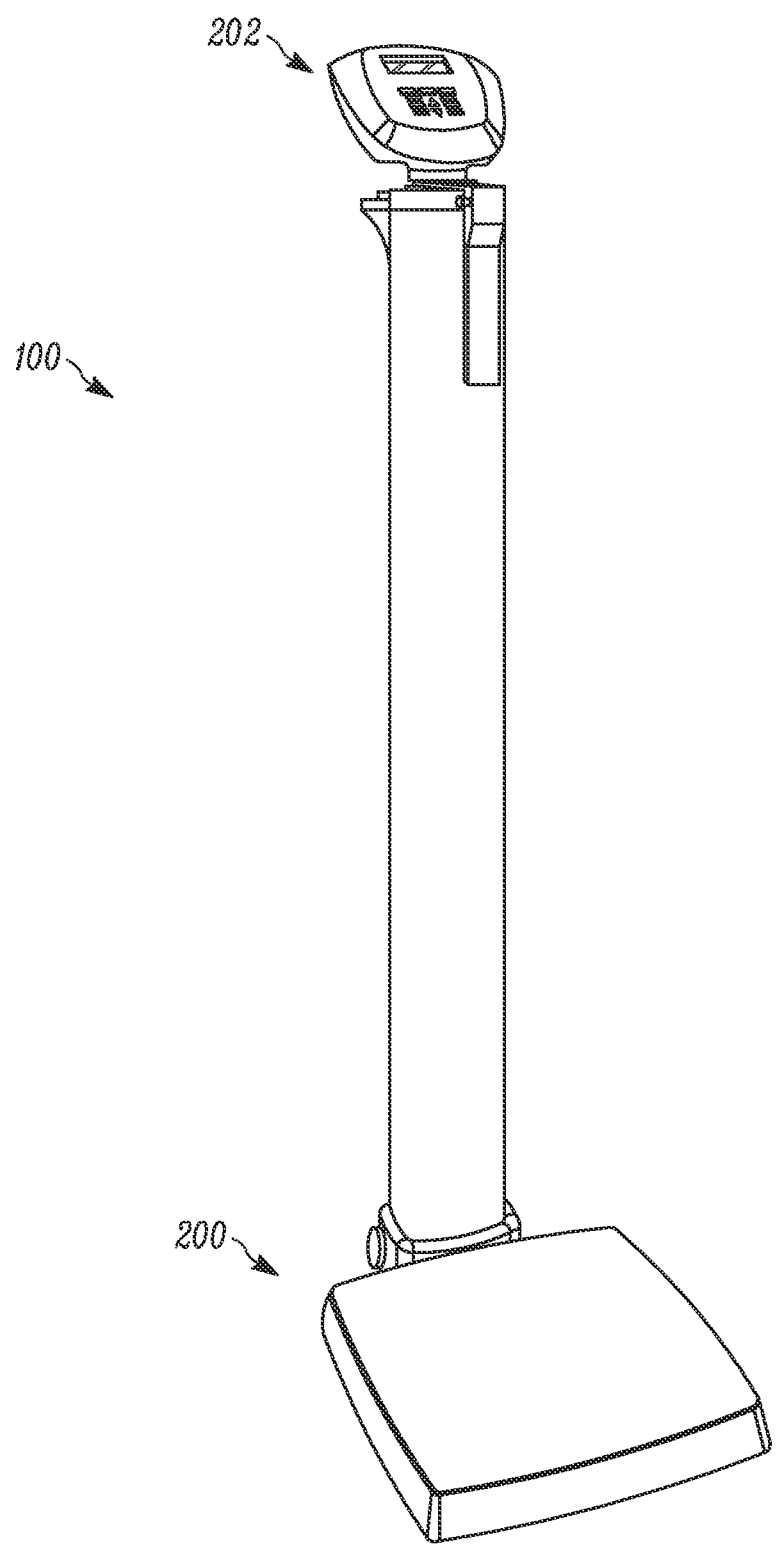

FIGS. 2A-2C illustrate constructions of the scale 100. As shown in FIG. 2A, a patient is positioned on a platform 200 of the scale 100, and the weight of the patient is displayed on a display of a head unit 202. The illustrated head unit 202 includes a housing containing the electronic processor 102, the memory 104, the input/output interface 106, the HMI 110, and the reset input 112. In some embodiments, the head unit 202 is removable from the scale 100. In some constructions (not shown), the head unit 202 is not attached directly to the scale 100. The load cell 108 is operably coupled to the platform 200 to determine the weight of a patient on the platform 200 and connected to the head unit 202 via a wired or wireless connection (not shown).

Returning to FIG. 1, the processor 102 obtains and provides information (for example, from the memory 104, the input/output interface 106, the load cell 108, the HMI 110, combinations thereof, etc.), and processes the information by executing one or more software instructions or modules, capable of being stored, for example, in a random access memory ("RAM") area of the memory 104 or a read only memory ("ROM") of the memory 104 or another non-transitory computer readable medium (not shown). The software can include firmware, one or more applications, program data, filters, rules, one or more program modules, and other executable instructions. The processor 102 is configured to retrieve from the memory 104 and execute, among other things, software related to the control processes and methods described herein.

The memory 104 can include one or more non-transitory computer-readable media, and includes a program storage area and a data storage area. The program storage area and the data storage area can include combinations of different types of memory, as described herein. In the embodiment illustrated, the memory 104 stores, among other things, an Everlock™ value 118 and calibration data 120 (both described in more detail below). In some embodiments, the Everlock™ value 118 and the calibration data 120 are stored in a non-volatile random-access memory (NVRAM) of the memory 104.

The input/output interface 106 is configured to receive input and to provide output to peripherals. The input/output interface 106 obtains information and signals from, and provides information and signals to, (for example, over one or more wired and/or wireless connections) devices both internal and external to the scale 100. For example, in some embodiments, the load cell 108 provides electrical signals to the processor 102 via the input/output interface 106.

Figure 3:
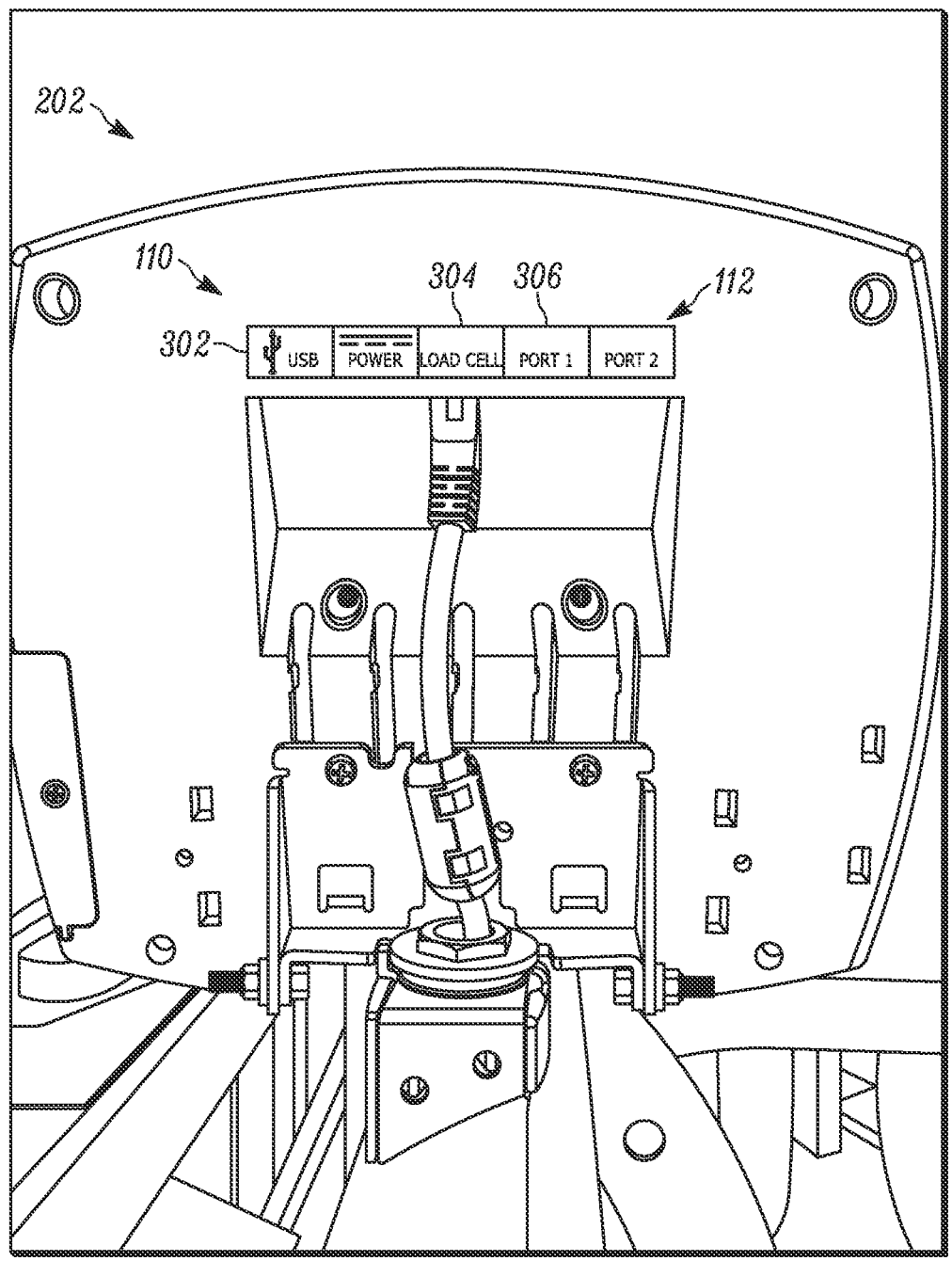
FIG. 3 illustrates an example embodiment of the input/output interface of the scale of FIG. 1.

In some embodiments, the input/output interface 106 (or portions thereof) is integrated with the processor 102. In some embodiments, the input/output interface 106 includes ports for connecting to wired connections. FIG. 3 illustrates an example embodiment of a portion of the input/output interface 106, integrated into the head unit 202, including a USB port 302, a load cell interface port 304, and an electronic port 306. In the illustrated embodiment, the reset input 112 is integrated with the input/output interface 106. Returning to FIG. 1, in some embodiments, the reset input 112 interfaces with a reset dongle 113 to allow portions of the memory 104 to be reconfigured, as described more particularly below.

As mentioned above, the scale 100 is used to measure the weight of a patient 114. The patient 114 stands on a platform 200 (See FIG. 2), which exerts the force of the patient's weight on the load cell 108. The illustrated load cell 108 includes a transducer, which produces electrical signals (for example, a voltage) in proportion to a force exerted on it. The processor 102 is configured to process the signals to calculate a weight for the patient 114. In some embodiments, the scale 100 is configured to provide the measured weight to an electronic medical records (EMR) system 116.

The HMI 110 receives input from, and provides output to, users of the scale 100. The HMI 110 may include a keypad, switches, buttons, soft keys, indictor lights (for example, light emitting diodes (LEDs), haptic vibrators, etc.). In some embodiments, the HMI 110 includes a suitable display, for example, a liquid crystal display (LCD) screen, an organic light-emitting diode (OLED) screen, etc. In some embodiments, the display is a touch screen display.

Figure 4:
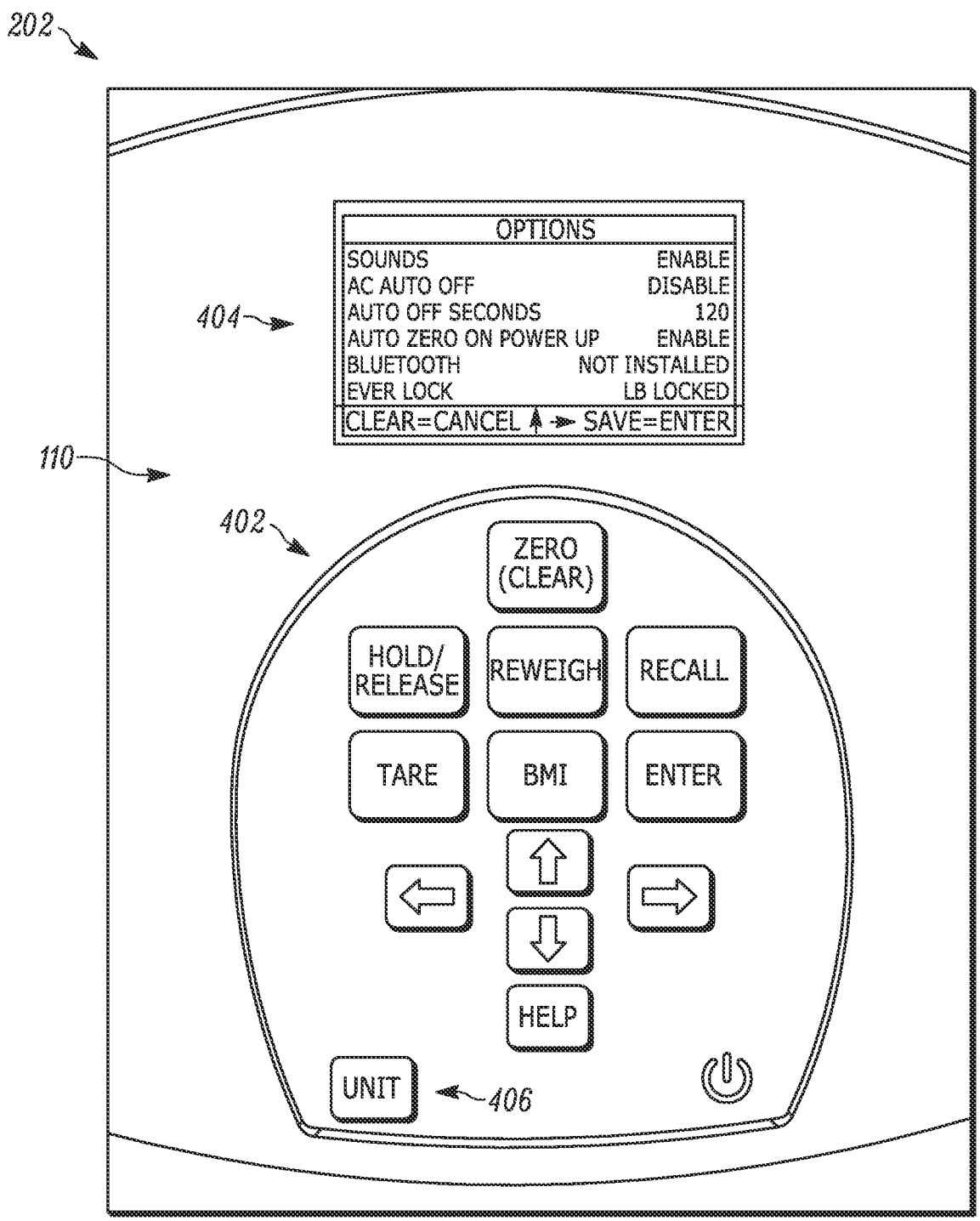
FIG. 4 illustrates an example embodiment of the human-machine interface of the scale of FIG. 1.

In some embodiments, the scale 100 implements a graphical user interface (GUI) (for example, generated by the processor 102, from instructions and data stored in the memory 104, and presented on the display of the HMI 110) enabling a user to interact with and control the scale 100, including the user terminal. In some embodiments, the HMI 110 presents a menu system for configuring and interacting with the scale 100. FIG. 4 illustrates an example embodiment of the HMI 110, integrated into the head unit 202, including a keypad 402 and an LCD display 404 implementing a menu system.

In some embodiments, one or more components of the HMI 110 are separate from the head unit 202, and are communicatively coupled with the head unit 202 (for example, via the input/output interface 106 using a wired or wireless connection). For example, in some embodiments, the HMI 110 may include a keypad and a display disposed in a separate hardware module, which is coupled to the head unit 202 (for example, via a wired connection to the input/output interface 106).

In some embodiments, one or more components of the HMI 110 may be presented virtually on another electronic device, which is in communication with the head unit 202. For example, a smart telephone or other computing device may include an application, which presents a virtual display and keypad (or other input means). In some embodiments, a combination of approaches is used. For example, a display may be integrated into the head unit 202, while a separate keypad may be attached for menu navigation and configuration of the scale. In some embodiments, access to some functions of the head unit 202 is restricted to either an integrated HMI 110 or a remote HMI 110. For example, certain menu functions (for example, activating the Everlock™ mode) may only be accessible using a remote HMI 110.

As noted above, the processor 102 implements software to allow users to operate the scale 100. In some embodiments, the software includes functions pertaining to the unit of measure used by the scale 100. In the illustrated construction and in some independent aspects, the scale 100 has multiple modes related to the measurement unit.

For example, in a "Toggle" mode, the user may select a unit of measurement (for example, pounds, kilograms, etc.). In a "Unit Lock" mode, the user may set the unit of measurement to one unit (for example, kilograms, pounds, etc.). In some modes (for example, the Toggle mode and the Unit Lock mode), the user may be able to temporarily view or display another unit (for example, pounds). In an Everlock™ mode, the user may "permanently" lock the unit of measurement.

In the "Toggle" mode, the scale 100 provides a "Unit Toggle" function. In such embodiments, pressing a button on the head unit 202 (for example, the "Unit" button 406 (see FIG. 4)) results in toggling the scale's measurement and display of weight between different units (for example, from one unit (kilograms) to another unit (pounds)).

Figure 5:
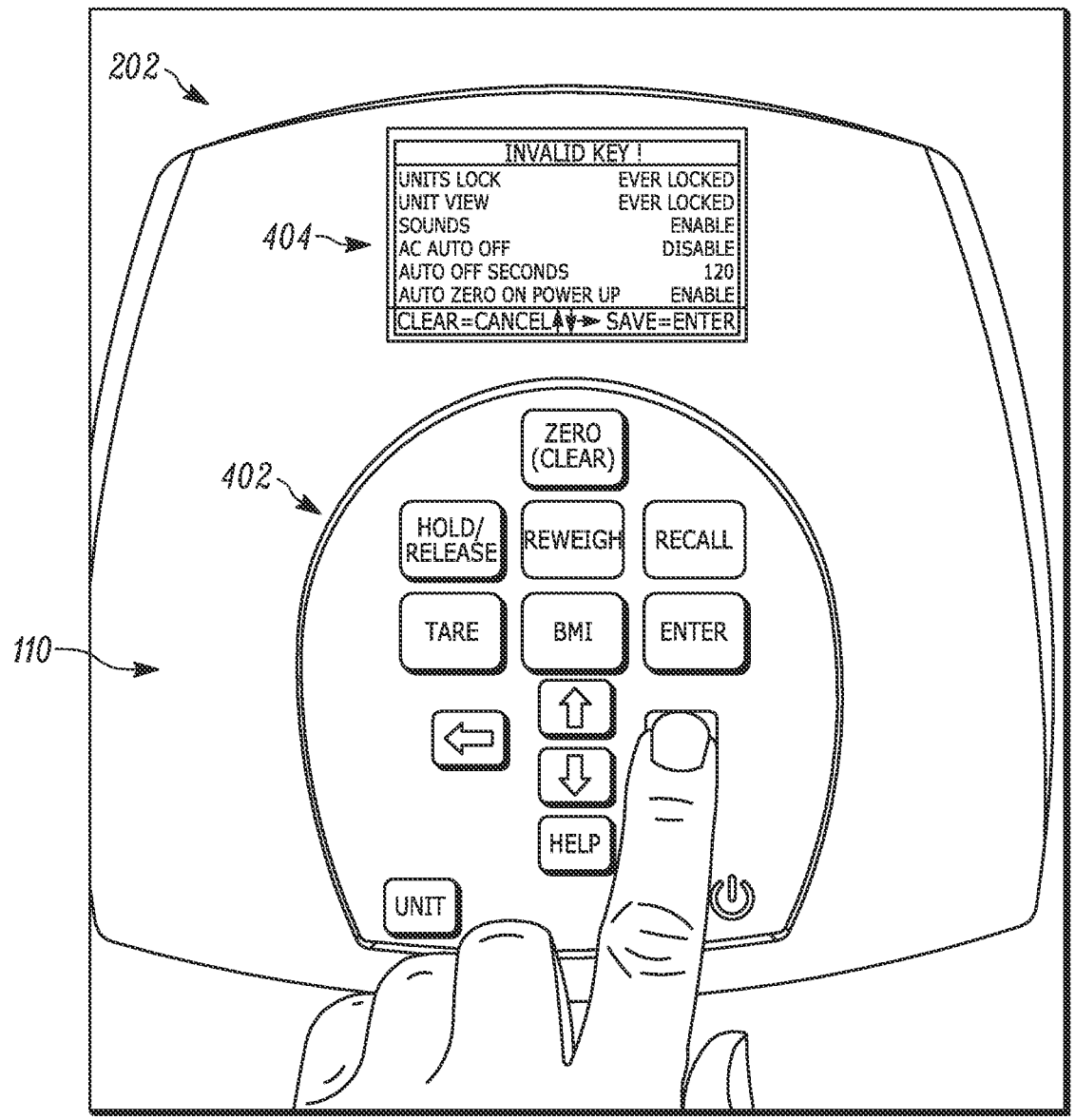
FIG. 5 illustrates an example embodiment of the human-machine interface of the scale of FIG. 1.

In the "Unit Lock" mode, a user of the scale 100 may navigate a menu on the display of the HMI 110 to select the Unit Lock function (see, for example, FIG. 5). No authentication is required to activate the Unit Lock function. Activating the Unit Lock function locks the scale 100 in one measurement unit (for example, kilograms or pounds). When the Unit Lock function is enabled, the Unit Toggle function is disabled. The Unit Lock function may be disabled (for example, by the user) through the menu system of the HMI 110.

In some modes, the scale 100 provides a "Unit View" function. With the Unit View function, after a patient has been weighed and while the weight is being displayed in one unit (for example, kilograms), pressing and holding a button on the head unit 202 (for example, the 'Unit' button 404) results in displaying the currently measured weight in another unit of measurement (for example, pounds). When the button is released, the display reverts to displaying the currently measured weight in the original unit (for example, kilograms).

As noted above, in some operating environments, it is desirable that the unit of measure be permanently locked, such that no display of the other unit, temporary or otherwise, is possible. Accordingly, in some aspects, the scale 100 provides an Everlock™ mode. Setting the scale to the Everlock™ mode causes the scale to be permanently locked into a selected unit of measure. In some embodiments, the Everlock™ mode is activated via a menu of the menu system of the HMI 110 (see, for example, FIG. 4).

Figure 6:
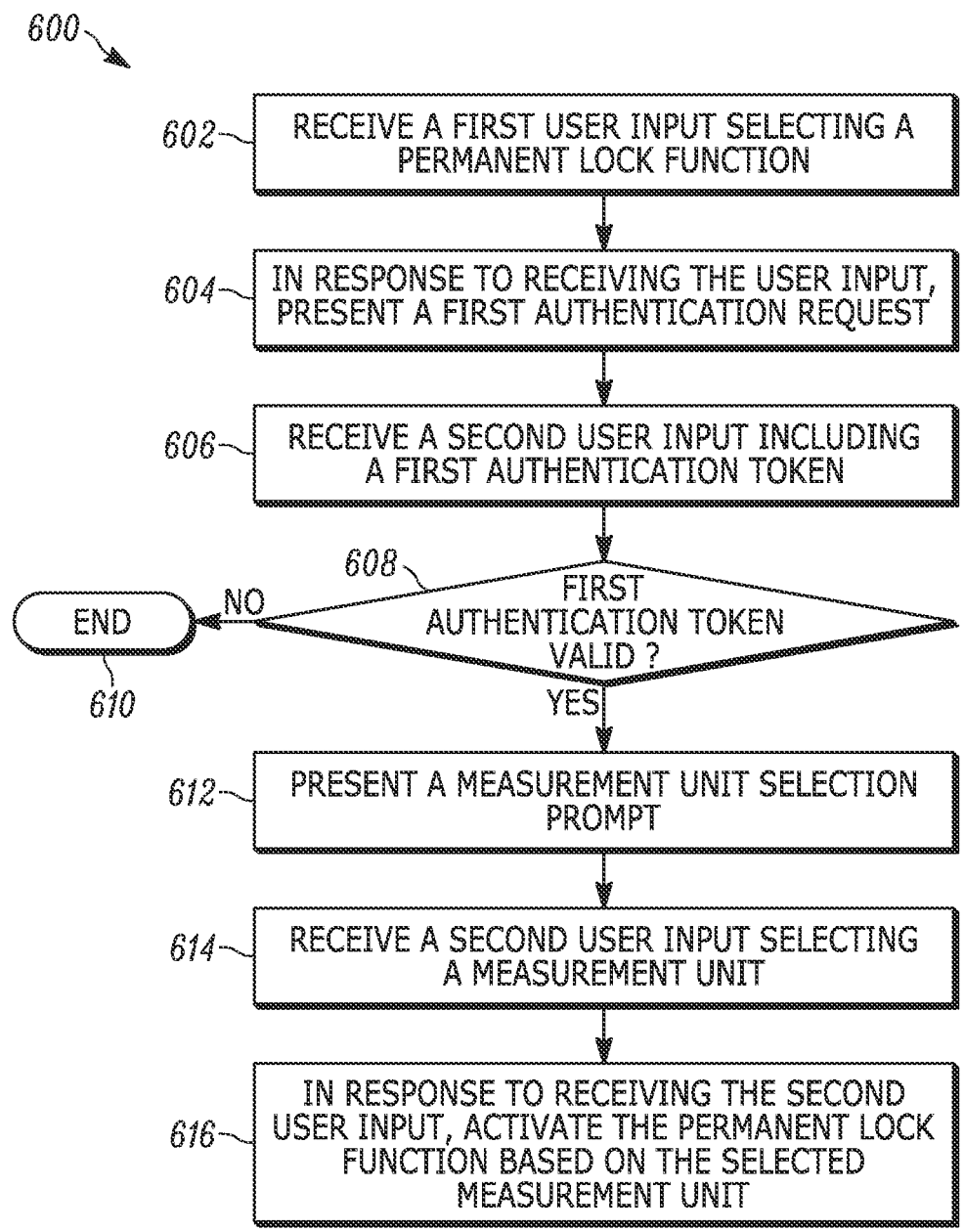
FIG. 6 is a flowchart illustrating a method of activating an Everlock™ mode for the scale of FIG. 1 according to some independent embodiments.

In some embodiments, the Everlock™ mode is activated using a multi-step process. FIG. 6 illustrates an example method 600 for activating the Everlock™ mode. As an example, the method 600 is described as being performed by the scale 100 and, in particular, the electronic processor 102.

At block 602, the electronic processor 102 receives, via the HMI 110, a first user input selecting a permanent lock (Everlock™) mode. For example, a user may select the Everlock™ mode from a menu system (as illustrated in FIG. 4). At block 604, in response to receiving the user input, before the user is allowed to proceed, the electronic processor 102 presents, via the HMI 110, a first authentication request. In some embodiments, the authentication request may include a prompt for the user to enter or present an authentication token.

At block 606, the electronic processor 102 receives a second user input including a first authentication token. In some embodiments, the authentication token is an alphanumeric password. In some embodiments, the authentication token may be a personal identification number (PIN), a biometric authentication (for example, a fingerprint scan), an RFID authentication, an NFC authentication, a security key insertion, etc.

In some embodiments, the electronic processor 102 receives a password or PIN via a keypad of the HMI 110. In some embodiments, the electronic processor 102 receives the authentication token from the input/output interface 106. For example, via an RFID scanner, key reader, fingerprint scanner, or other input device coupled to the input/output interface 106.

At block 608, the electronic processor 102 determines whether the first authentication token is valid. The authentication token is considered valid if the user enters the correct authentication for that particular authentication request. In some embodiments, when the authentication token is invalid, the user is not authorized to enable the permanent lock mode, and the method 600 ends, at block 610. At block 608, when the authentication token is valid, the electronic processor 102 presents, via the HMI 110, a measurement unit selection prompt, at block 612. This prompt allows the user to toggle between units to select the preferred unit, for example, by using arrow keys on the keypad 402 of the HMI 110 (as illustrated in FIG. 4).

At block 614, the electronic processor 102 receives, via the HMI 110, a second user input selecting a measurement unit. At block 616, in response to receiving the second user input, the electronic processor 102 activates the permanent lock (Everlock™) mode based on the selected measurement unit. In some embodiments, in response to activating the permanent lock mode, the electronic processor 102 causes the HMI 110 to display a message (for example, "Everlock KG Locked," "Everlock LB Locked," etc.) indicating that the scale 100 is permanently locked into the selected unit.

In some embodiments, the electronic processor 102 activates the Everlock™ mode by setting the Everlock™ value 118 in an NVRAM of the memory 104 of the scale 100. In some embodiments, software functions of the scale 100 may be programmed to reference the Everlock™ value 118 prior to displaying units or activating features or functions pertaining to units. When the Everlock™ value 118 is set to "active," such software functions are configured to display or provide weight in only the locked units. In some embodiments, no code is provided that is able to write to the Everlock™ value 118 once set, and all code pertaining to the Everlock™ value 118, other than the activation routines, is read only code. This helps to ensure that the Everlock™ mode is permanently set.

In some embodiments, when the Everlock™ mode is activated, the Unit Toggle, Unit Lock, and Unit View functions are disabled. In some embodiments, this condition is reflected in the menu system of the HMI 110. For example, with the Everlock™ mode activated, the menu items corresponding to those features indicate that the features are "Everlocked" (see, for example, FIG. 5), while in another example, these menu items do not display at all. In some embodiments, the Unit button is disabled (that is, pressing the Unit button has no effect).

In some embodiments, confirmation is required to activate the permanent lock mode. For example, in response to receiving the second user input, the electronic processor 102 presents, via the HMI 110, a confirmation prompt (for example, "Warning! This will lock the Units permanently. This cannot be reversed."). The electronic processor 102 receives, via the HMI 110, a third user input. When the third user input confirms the selection of the permanent lock mode, the electronic processor activates the permanent lock mode based on the selected measurement unit.

In some embodiments, a second authentication is required to activate the permanent lock mode. In such embodiments, the confirmation prompt includes a second authentication prompt, and the third user input includes a second authentication token. Only when the first and second authentication tokens are valid does the electronic processor 102 activate the Everlock™ mode.

In some embodiments, a confirmation prompt may be generated via the HMI 110 in response to a successful entry of the second authentication. In such embodiments, a user input confirming the selection of the permanent lock mode is required to activate the permanent lock mode based on the selected measurement unit.

In some embodiments, to add extra protection against inadvertent activation of the permanent lock mode, the second authentication token is different than the first authentication token. The second authentication token may be different from the first authentication token in either value or form. For example, in the case of differing values of authentication, the first authentication token may be a password while a second authentication token may also be a password with a different value (for example, a first password may contain a first arrangement of alphanumeric characters while a second password may contain a second arrangement of alphanumeric characters). In another example, in the case of differing forms of authentication, a first authentication may be a password and a second authentication may be a card scan. These embodiments are not meant to be limiting but rather to provide examples of ways that the first and second authentication means may differ. In some embodiments, the user may exit the permanent lock mode activation process at any time prior to successfully entering the second authentication.

In some embodiments, activation of the permanent lock mode may only take place after more than two confirmation prompts are presented to the user, and answered with the correct responses (for example, an affirmative response or a valid authentication token).

Returning to FIG. 1, to provide scales that may be re-deployed to uses in which the display of a unit other than the "Everlocked" unit is required or desired, some embodiments provide a scale 100 with an Everlock™ mode that may be unlocked in a limited number of ways (that is, is factory-resettable). In some embodiments, the Everlock™ value 118 may only be erased when the reset dongle 113 is present. In some embodiments, the electronic processor 102 is configured to check for the presence of the reset dongle 113 upon power up by detecting whether the reset dongle is attached to the input/output interface 106. In such embodiments, when the presence of the reset dongle 113 is detected, the electronic processor 102 enters a factory mode. The factory mode, among other things, allows the Everlock™ value 118 to be reset (for example, by a technician in the factory) using the menu system of the HMI 110.

In some embodiments, the reset dongle 113 includes circuits, which present particular electrical characteristics (for example, a voltage, a resistance, a capacitance, a resonance, an inductance, or combinations thereof) at the reset input 112. In such embodiments, when the electronic processor 102 detects those particular characteristics, the electronic processor 102 enters the factory mode.

In some embodiments, the reset dongle 113 functions using pin shorting. In such embodiments, when the electronic processor 102 detects the correct pin shorting sequence, the processor 102 enters the factory mode.

In some embodiments, the software code for resetting the Everlock™ value 118 (the factory mode) resides only on the reset dongle 113 (for example, in a UICC or other non-volatile storage). In such embodiments, the presence of the reset dongle 113 prompts the electronic processor 102 to activate reset software on the reset dongle 113. In some embodiments, the reset dongle 113 is a one-time use device. For example, the reset dongle 113 may be configured to erase any software code for resetting the Everlock™ value 118 after the code is used to reset the Everlock™ value 118. In another example, the reset input 112 is configured to provide an electrical current to the reset dongle 113 sufficient to alter the electrical characteristics of the reset dongle 113.

Regardless of how the Everlock™ value 118 is reset, the reset procedure leaves the calibration data 120 unaltered, preserving the scale's calibration settings. The Everlock™ value 118 may be reset by "re-flashing" or overwriting a portion of the memory 104 in which the Everlock™ value 118 is stored while other portions of the memory 104 are not re-flashed or overwritten and are, thus, maintained. Accordingly, a scale 100 may be reset from Everlock™ mode to multi-unit functioning without requiring recalibration. Once the scale 100 is unlocked, the scale 100 may be operated to any of the modes, including the Everlock™ mode.

Thus, the invention may provide, among other things, systems and methods for permanently locking medical scales into a measurement unit (for example, kilograms or pounds) while allowing factory reset and maintaining the scale's calibration. The medical scale may also be operable in more than one mode relating to the unit of measurement.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

One or more independent features and/or independent advantages of some embodiments may be set forth in the following claims:

What is claimed is:

1. A system for controlling measurement units for a medical scale, the system comprising:
   a removable head unit configured to couple to a medical scale platform, the removable head unit including a memory, a human machine interface, an input/output interface, and an electronic processor coupled to the memory, the human machine interface, and the input/output interface, and configured to:
   receive, via the human machine interface, a first user input selecting a permanent lock mode;
   in response to receiving the first user input selecting the permanent lock mode, present, via the human machine interface, a measurement unit selection prompt;
   in response to presenting the measurement unit selection prompt, receive, via the human machine interface, a second user input selecting a measurement unit;
   in response to receiving the second user input selecting the measurement unit, activate the permanent lock mode based on the selected measurement unit by setting a value in the memory;
   detect a reset dongle attached to the input/output interface; and
   in response to detecting the reset dongle, deactivate the permanent lock mode by erasing the value without altering scale calibration data stored in the memory.

2. The system of claim 1, wherein the electronic processor is further configured to:
   in response to receiving the second user input, present, via the human machine interface, a confirmation prompt;
   receive, via the human machine interface, a third user input; and
   when the third user input confirms the selection of the permanent lock mode, activate the permanent lock mode based on the selected measurement unit.

3. The system of claim 1, wherein the electronic processor is further configured to:
   in response to receiving the first user input selecting the permanent lock mode, present, via the human machine interface, a first authentication request;
   in response to presenting the first authentication request, receive, via the human machine interface, a third user input including a first authentication token; and activate the permanent lock mode only in response to receiving the first authentication token and when the first authentication token is valid.

4. The system of claim 3, wherein receiving the first authentication token includes receiving a first authentication token selected from a group consisting of an alphanumeric password, a personal identification number, a biometric authentication, a Radio Frequency Identification (RFID) authentication, a Near Field Communication (NFC) authentication, and a security key insertion.

5. The system of claim 1, wherein the electronic processor is further configured to:
   in response to activating the permanent lock mode, disable at least one function selected from a group consisting of a unit toggle function, a unit lock function, and a unit view function.

6. The system of claim 1, wherein the electronic processor is further configured to:
   generate, on the human machine interface, a graphical user interface including a menu system; and
   receive the first user input by receiving the user input via the menu system.

7. The system of claim 6, wherein the electronic processor is further configured to:
   in response to activating the permanent lock mode, display, in the menu system, a locked indication for menu items corresponding to at least one function selected from a group consisting of a unit toggle function, a unit lock function, and a unit view function.

8. A method for controlling measurement units for a medical scale, the method comprising:
   receiving, via a human machine interface, a first user input selecting a permanent lock mode;
   in response to receiving the first user input, presenting a measurement unit selection prompt;
   receiving a second user input selecting a measurement unit;
   in response to receiving the second user input, activating, with an electronic processor, the permanent lock mode based on the selected measurement unit by setting a value in a memory of the medical scale;
   detecting a reset dongle attached to the input/output interface; and
   in response to detecting the reset dongle, deactivating the permanent lock mode by erasing the value without altering scale calibration data stored in the memory.

9. The method of claim 8, further comprising:
   in response to receiving the second user input, presenting, a confirmation prompt;
   receiving, via the human machine interface, a third user input; and
   when the third user input confirms the selection of the permanent lock mode, activating the permanent lock mode based on the selected measurement unit.

10. The method of claim 8, further comprising:
    in response to receiving the first user input selecting the permanent lock mode, presenting, via the human machine interface, a first authentication request;
    in response to presenting the first authentication request, receiving, via the human machine interface, a third user input including a first authentication token; and
    activating the permanent lock mode only in response to receiving the first authentication token and when the first authentication token is valid.

11. The method of claim 10, wherein receiving the first authentication token includes receiving a first authentication token selected from a group consisting of an alphanumeric password, a personal identification number, a biometric authentication, an RFID authentication, an NFC authentication, and a security key insertion.

12. The method of claim 8, further comprising:
    in response to activating the permanent lock mode, disabling at least one function selected from a group consisting of a unit toggle function, a unit lock function, and a unit view function.

13. The method of claim 8, further comprising:
    generating, on the human machine interface, a graphical user interface including a menu system; and
    receiving the first user input by receiving the user input via the menu system.

14. The method of claim 13, further comprising:
    in response to activating the permanent lock mode, displaying, in the menu system, a locked indication for menu items corresponding to at least one function selected from a group consisting of a unit toggle function, a unit lock function, and a unit view function.

15. A removable head unit for a scale, the removable head unit comprising:
    a memory;
    an input/output interface; and
    an electronic processor coupled to the memory and the input/output interface, and configured to:
    detect a reset dongle attached to the input/output interface; and
    deactivate the permanent lock mode by resetting a permanent lock mode value in the memory without altering scale calibration data stored in the memory.

16. The removable head unit of claim 15, wherein the electronic processor is further configured to, in response to detecting the reset dongle, activate a reset software on the reset dongle.

17. The removable head unit of claim 15, further comprising a human machine interface, wherein the electronic processor is further configured to:
    in response to detecting the reset dongle, enter a factory mode;
    receive, via the human machine interface, a first user input; and
    deactivate the permanent lock mode in response to receiving the first user input.

18. The removable head unit of claim 15, further comprising a human machine interface, wherein the electronic processor is further configured to:
    receive, via the human machine interface, a first user input selecting the permanent lock mode;
    in response to receiving the first user input selecting the permanent lock mode, present, via the human machine interface, a measurement unit selection prompt;
    in response to presenting the measurement unit selection prompt, receive, via the human machine interface, a second user input selecting a measurement unit;
    in response to receiving the second user input selecting the measurement unit, activate the permanent lock mode based on the selected measurement unit by setting the permanent lock mode value in the memory.

19. The removable head unit of claim 18, wherein the electronic processor is further configured to:
    in response to receiving the second user input, present, via the human machine interface, a confirmation prompt;
    receive, via the human machine interface, a third user input; and
    when the third user input confirms the selection of the permanent lock mode, activate the permanent lock mode based on the selected measurement unit.

20. The removable head unit of claim 18, wherein the electronic processor is further configured to:
  in response to receiving the first user input selecting the permanent lock mode, present, via the human machine interface, a first authentication request;
  in response to presenting the first authentication request, receive, via the human machine interface, a third user input including a first authentication token; and
  activate the permanent lock mode only in response to receiving the first authentication token and when the first authentication token is valid.

\* \* \* \* \*